US005750862A

United States Patent [19]
John

[11] Patent Number: 5,750,862
[45] Date of Patent: May 12, 1998

[54] CONTROL OF PLANT CELL PROLIFERATION AND GROWTH

[75] Inventor: Peter Crook Lloyd John, Farrer, Australia

[73] Assignee: The Australian National University, Acton, Australia

[21] Appl. No.: 66,092

[22] PCT Filed: Nov. 29, 1991

[86] PCT No.: PCT/AU91/00556

§ 371 Date: Jun. 1, 1993

§ 102(e) Date: Jun. 1, 1993

[87] PCT Pub. No.: WO92/09685

PCT Pub. Date: Jun. 11, 1992

[30] Foreign Application Priority Data

Nov. 29, 1990 [AU] Australia ............................. PK 3584

[51] Int. Cl.$^6$ ..................... C12N 15/82; C12N 15/29; A01H 4/00; A01H 5/00
[52] U.S. Cl. ..................... 800/205; 800/DIG. 9; 800/DIG. 52; 536/23.6; 536/24.1; 435/172.3; 435/320.1; 435/419
[58] Field of Search ..................... 435/172.1, 172.2, 435/172.3, 240.1, 240.4, 240.47, 240.48, 240.49, 240.5, 419, 320.1; 800/200, 205, 220, 250, 255, DIG. 58, DIG. 9, DIG. 52; 536/23.6, 24.1

[56] References Cited

U.S. PATENT DOCUMENTS

| 5,015,580 | 5/1991 | Christou et al. | 435/172.3 |
| 5,187,073 | 2/1993 | Goldman et al. | 435/172.3 |
| 5,225,341 | 7/1993 | Yoder et al. | 435/172.3 |

FOREIGN PATENT DOCUMENTS

| 0 240 208 | 10/1986 | European Pat. Off. |
| 89/00319 | 10/1989 | WIPO . |
| WO90/02172 | 3/1990 | WIPO . |

OTHER PUBLICATIONS

Napoli et al. The Plant Cell, vol. 2 279–289 Apr. 1990 Introduction of a Chimeric Chalcone Synthase Gene ... Apr. 1990.
Smith et al. Nature, vol. 334 pp. 724–726 Aug. 1988 Antisense RNA Inhibition of Polygalacturonidase Gene ... Aug. 1988.
Potrykus. 1991. Annu. Rev. Plant Physiol. Plant Mol. Biol 42:205–225.
Finnegon et al. 1994. Bio/Technology. 12:883–888.
Derg, Jan., 1990. Science in China (Series B), 33(1): 27–34.
Draetta. 1990. Trends in Biochemical Science. 15:378–383.
Nurse, 5 Apr. 1990. Nature. 344: 503–507.
Lohka, 1989, Journal of Cell Science. 92:131–135.
Brizuela et al. 1987, The EMBO Journal, 6(11):3507–3514.
Russell et al. 1987, Cell, 49:569–576.
Wernicke et al. 1987, Physiol. Plantarum, 69:23–28.

John et al. 1989, The Plant Cell, 1:1185–1193.
Barwale et al. 1986, Planta, 167:473–481.
Redway et al. 1990, Theor. Appl. Genet. 79:609–617.
Feiler et al. Jul. 1990, Proc. Natl. Acad. Sci. USA, 87:5397–5401.
Schmidt et al., (1991) Peptide Proline Hydroxylation and the Growth of a Soybean Cell Culture, *Plant Physiol.* 96: 656–659.
Feiler et al. (1990) "Cell Division in Higher Plants: A cdc2 Gene, its 34–kDa Product, and Histone H1 Kinase Activity in Pea" *Proc. Natl. Acad. Sci. USA* 87:5397–5401.
Schmidt et al. (1991) "Peptidyl Proline Hydroxylation and the Growth of a Soybean Cell Culture" *Plant Physiol.* 96:656–659.
Feiler et al. (1991) "Cloning of the Pea cdc2 Homologue by Efficient Immunological Screening of PCR Products" *Plant Molecular Biology* 17:321–333.
Nurse et al. (1981) "Gene Required in $G_1$ for Commitment to Cell Cycle and in $G_2$ for Control of Mitosis in Fission Yeast" *Nature* 292:558–560.
Nurse et al. (1981) "Cell Cycle Controls in Fission Yeast: A Genetic Analysis" in *The Cell Cycle*, Cambridge University Press, Vail–Ballow Press, Inc., Binghamton, NY, 85–98.
Russell et al. (1987) "The Mitotic Inducer nim1+ Functions in a Regulatory Network of Protein Kinase Homologs Controlling the Initiation of Mitosis" *Cell* 49:569–576.
Moreno et al. (1990) "Regulation of Mitosis by Cyclic Accumulation of $p80_{cdc25}$ Mitotic Inducer in Fission Yeast" *Nature* 344:549–552.
Wernicke et al. (1987) "Rates of Uptake and Metabolism of Indole–3–Acetic Acid and 2,4–Dichlorophenoxyacetic Acid by Cultured Leaf Segments at Different Stages of Development in Wheat" *Physiol. Plantarum* 69:23–28.
John et al. (1989) "A Homolog of the Cell Cycle Control Protein $p34^{cdc2}$ Participates in the Division Cycle of *Chlamydomonas*, and a Similar Protein is Detectable in Higher Plants and Remote Taxa" *The Plant Cell* 1:1185–1193.
Lee et al. (1987) "Complementation Used to Clone a Human Homologue of the Fission Yeast Cell Cycle Control Gene cdc2" *Nature* 327:31–35.

(List continued on next page.)

*Primary Examiner*—Douglas W. Robinson
*Assistant Examiner*—Thomas Haas
*Attorney, Agent, or Firm*—Scully, Scott, Murphy & Presser

[57] ABSTRACT

The present invention is directed to a method for controlling plant cell growth comprising modulating the level and or catalytic activity of a cell cycle control protein in said plant cell for a time and under conditions sufficient to control cell division. Preferably, the cell cycle control protein is $p34^{cdc2}$ or like molecule and the plant is a monocotyledonous plant or dicotyledonous plant.

4 Claims, 6 Drawing Sheets

OTHER PUBLICATIONS

Snyder et al. (1987) "λgt 11 Gene Isolation with Antibody Probes and Other Applications" *Methods in Enzymology* 154:107–127.

Toh–e et al. (1988) "PHO85, a Negative Regulator of the PHO System, is a Homolog of the Protein Kinase Gene, CDC28, of *Saccharomyces cerevisiae*" *Molecular General Genetics* 214(1):162–163.

Wernicke et al. (1987) "Effect of Auxin on the Mitotic Cell Cycle in Cultured Leaf Segments at Different Stages of Development in Wheat" *Physiol. Plantarum* 69:16–22.

John et al. (1991) "Association of the Plant $P34^{cdc2}$–like Protein with $p13^{suc1}$: Implications for Control of Cell Division Cycles in Plants" *Protoplasma* 161:70–74.

Gorst et al. (1991) "Levels of $p34^{cdc2}$–like Protein in Dividing, Differentiating and Dedifferentiating Cells of Carrot" *Planta* 185:304–310.

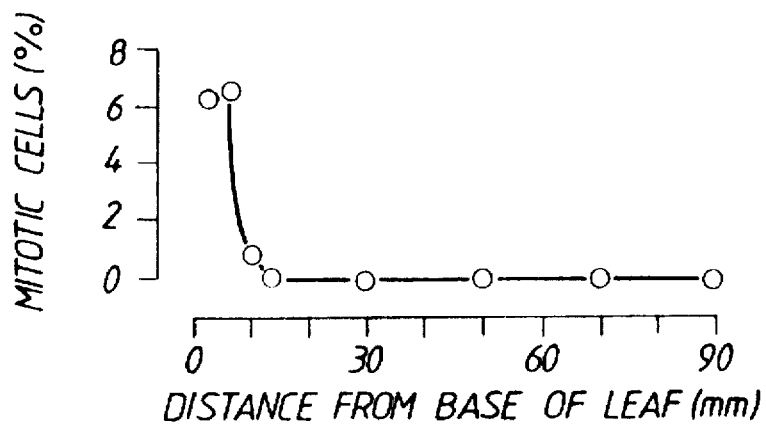
Fig.2A.
Fig.2B
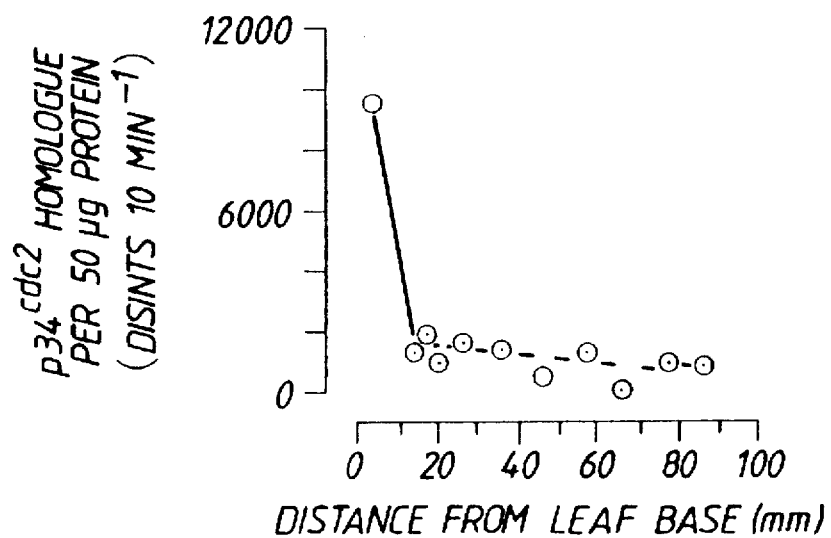
Fig.8.

DISTANCE FROM LEAF BASE (mm)

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 16 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

```
Glu  Gly  Val  Pro  Ser  Thr  Ala  Ile  Arg  Glu  Ile  Ser  Leu  Leu  Lys  Glu
 1              5                        10                          15
```

( 2 ) INFORMATION FOR SEQ ID NO:2:

( i ) SEQUENCE CHARACTERISTICS:
        ( A ) LENGTH: 16 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:2:

```
Glu Gly Thr Pro Ser Thr Ala Ile Arg Glu Ile Ser Leu Met Lys Glu
 1               5                   10                  15
```

CONTROL OF PLANT CELL PROLIFERATION AND GROWTH

FIELD OF THE INVENTION

The present invention relates generally to a method for controlling plant cell growth. More particularly, the present invention is directed to controlling plant cell proliferation and differentiation by modulating the levels of a cell cycle control protein or modulating its activity by altering the levels of enzymes that act upon it.

BACKGROUND OF THE INVENTION

The formation of a plant involves the generation of new cells by the division cycle and development in these of specialised structure and metabolism. specialization is accompanied by a decreasing capacity for division which declines with particular rapidity in cells of monocotyledonous plants, such as cereals.

In yeast, cdc2 gene function is necessary for progress through the two major control points at which the cell cycle can be delayed until the requirements of cell size and nutrition are met (1; 2). The control of these points is effected by the interaction of the cdc2 gene product, $p34^{cdc2}$, with stimulatory and inhibitory elements (3; 4).

The possible contribution of changing $p34^{cdc2}$ level to control of cell division during development has been little studied in any organism.

SUMMARY OF THE INVENTION

In accordance with the present invention, it has now been discovered that in the leaves of a cereal plant, a homologue of $p34^{cdc2}$ participates in the control of cell division and development. Modulation of expression and/or activity of this protein will enable control of cell proliferation and differentiation and facilitate such processes as plant regeneration and development.

Accordingly, one aspect of the present invention contemplates a method for controlling plant cell growth comprising modulating the level and/or catalytic activity of a cell cycle control protein in said plant for a time and under conditions sufficient to modify or control cell division.

DETAILED DESCRIPTION OF THE INVENTION

In accordance with this aspect of the present invention, "plant cell" means any cell existing in culture as a single cell or a group of cells or as a callus. The cells may also be in a developing plant in culture or may be in a plant growing in nature. The plant cell may be naturally occurring or isolated from a plant or may be a recombinant, mutant or otherwise derivatized plant cell or group of cells. The plant may be either dicotyledonous or monocotyledonous and in the latter case, the cell cycle genes may be additionally used in an initial phase that aids regeneration from protoplast cells. This additional technique to aid resumption of division will be particularly valuable when applied to wheat, barley, oats, maize, rice and other like crops.

For the monocotyledonous plants the present invention has a double advantage: (1) making regeneration from protoplasts easier after the introduction of any beneficial gene; and (2) the addition of cell cycle genes to the plant's genotype. For dicotyledonous plants, advantage (2) particularly applies, since they are already easily regenerable.

Preferably, the cell cycle control protein is $p34^{cdc2}$ including its derivatives, homologues and functional analogues. This protein may be homologous to the plant cell being controlled, i.e. is naturally occurring in said cell or may be heterologous to the cell, i.e. the protein or its genetic sequences may be introduced into the cell from a source not originating from the same plant. For example, the control protein may be from another plant or may be from another eukaryotic cell, such as a yeast cell. The $p34^{cdc2}$ protein or like molecule may also be a hybrid of molecules and/or be encoded by a hybrid genetic sequence. Use herein of the term "$p34^{cdc2}$ or like molecule" encompasses all such homologous or heterologous derivatives, homologues and functional analogues. The present invention extends to other cell cycle control proteins, so termed since they function similarly to $p34^{cdc2}$ or control $p34^{cdc2}$ activity. Such proteins include $p13^{suc1}$, cyclin, cdc25, and the products of nim-1, wee-1 and mik-1 or combinations thereof, separately or together with $p34^{cdc2}$. By "derivatives" of $p34^{cdc2}$ is meant any protein molecule having an amino acid sequence which differs by at least one amino acid compared to the sequence in the naturally occurring molecule before derivatisation. Additionally, the term refers to recombinant or synthetic molecules and molecules carrying single or multiple amino acid substitutions, deletions and/or additions or any substitution, deletion and/or addition of an associated molecule such as a carbohydrate or lipid moiety.

Conveniently, the level of $p34^{cdc2}$ may be controlled at the genetic level by manipulating the cdc2 gene promoter (or its equivalent). For example, a different promoter may be inserted which can be developmentally regulated or regulated by some other means. Use of a different promoter may provide an opportunity for enhanced expression and/or greater control of expression. Alternatively, multiple copies of a homologous or heterologous cdc2 gene under suitable control may be inserted to increase the level of expression. It would also be possible to manipulate control genes or genetic sites which assist in or regulate expression of the cdc2 gene. One skilled in the art will immediately recognize the variety of means to control expression of a homologous and/or heterologous cdc2 gene in vivo such as the use of antisense or ribozyme agents to reduce expression of inhibitory genes and all such means are encompassed within the scope of the present invention. For example, the cell cycle protein, such as $p34^{cdc2}$ may be controlled at the level of activity of enzymes which act upon the cell cycle protein.

The $p34^{cdc2}$ levels may also be controlled at the protein level. Such a control is more applicable to growth of cells in vitro but the present invention is not necessarily so limited. In accordance with this aspect of the present invention, the cell cycle control protein, for example, is added to a culture and permeated into the cells by various procedures such as electroporation. Purification of the protein into a suitable form as been described (12). An amount is used for a time and under conditions sufficient to modulate cell growth.

In relation to the method for controlling plant growth, this may involve the stable integration of cell cycle genes into the plant genome under the control of promoters that can be expressed at appropriate locations and times, such as in early seed development and at meristems. This may be done in dicotyledonous crop plants by conventional methods of transformation, such as with Agrobacterium. It may also be done in monocotyledonous plants using published procedures such as biolistic microprojectile bombardment to introduce genes into cells derived from embryogenic callus followed by regeneration.

Another aspect of the invention is to use cell cycle genes to increase the number of monocotyledonous plants that can be transformed and the ease with which any monocotyledonous plant can be transformed, by making it unnecessary to carry out prolonged suspension culture.

Depending on the plant cells involved, the cell membrane may have to be treated and/or the protein itself may have to be derived in order to facilitate entry into the target cell. Alternatively, inhibitors, antagonists or agonists of the activity of the cycle control protein may be used. Furthermore, a combination of such procedures may also be employed. In one particular embodiment, $p34^{cdc2}$ is used in combination with an auxin.

In accordance with the present invention, therefore, it has been discovered that the amount of $p34^{cdc2}$ is limiting for cell division in plant tissue. When cessation of division for development of specialised functions is required, this is determined by the decline to low levels of this key cell cycle control protein. In tissues that are able to resume cell division, this protein is induced prior to division (12). Furthermore, the present inventors have discovered that plant $p34^{cdc2}$ interacts with a regulatory subunit $p13^{suc1}$ from fission yeast which plays a part in controlling the activity of yeast $p34^{cdc2}$ A plant homologue of $p13^{suc1}$ has now been found. The function of $p13^{suc1}$ is necessary for completion of mitosis in fission yeast. The fact that the plant $p34^{cdc2}$ protein associates with one regulatory subunit implies that the other regulatory interactions identified genetically in yeasts may operate in plants and that the regulatory genes, taken initially from yeasts, could be used to control plant cell division. Accordingly, the present invention extends not only to the direct control of $p34^{cdc2}$ levels but also to the control of regulatory elements such as $p13^{suc1}$, wee-1, mik-1, nim-1 and cdc25 which indirectly result in modulation of $p34^{cdc2}$ activity.

The present invention will be particularly useful in the regeneration of plants. The mature cells of wheat leaf, for example, yield robust protoplasts that are most suitable for the introduction of DNA but they are notoriously difficult to regenerate into plants. It has now been discovered that these cells have low levels of $p34^{cdc2}$ and are not capable of increasing these levels. This appears to be a fundamental difference in organization between monocotyledonous plants and dicotyledonous plants. In the latter group, growth is apical and wounding results in the generation of new meristem cells capable of restoring new tissue. In the monocotyledonous plants, however, there are no terminal meristems and growth is by the continued division of basal meristems. Wounding does not result in the establishment of localised meristems. Accordingly, by elevating levels of $p34^{cdc2}$ regeneration into plants of single or groups of cells can be facilitated.

A particular application is the influence of division activity in transformed monocotyledonous protoplasts to enhance their division when the cells have not previously undergone prolonged propogation in suspension culture. For this purpose the influence on division need only be transient and nonintegrative genetic transformation, or introduction of the protein, would be suitable. This use would make it easier to introduce any beneficial gene into monocotyledonous plants.

The use of cell cycle proteins or genetic sequences encoding same to facilitate resumption of division after protoplasting of cells will allow the introduction into monocotyledonous plants of genes that are to be stably integrated into the genome. The introduced genes include those conferring improvements in increased temperature range for growth, disease resistance, water utilization, grain size and growth under adverse conditions.

With reference to the latter, the present invention also contemplates a method for modifying plant growth behaviour in the presence of one or more environmental conditions, said method comprising modulating the level of a cell cycle protein in one or more plant cells capable of division in said plant for a time and under conditions sufficient for said plant to modify its growth. Preferably, the plant is a monocotyledonous plant such as wheat, barley, oats, maize, rice or other like crop and the cell cycle protein is $p34^{cdc2}$ or like molecule. The term "environmental condition" is used in its broadest sense to include such conditions as growth under increased or decreased temperatures, exposure to disease and excess or insufficiency of water or other nutrient.

In connection with grain size and growth, genes introduced for stable integration would include cell cycle control genes. In this case genes promoting division would be used in two ways during the overall process: 1. during the phase of resumption of division after protoplasting transient expression of the genes, or introduction of the proteins that they encode, would be used to reinitiate division; 2. additional cell cycle genes introduced in DNA also containing a transposable element such as Ac and a selectable marker, such as neo, would be stably integrated and used to modify division activity in the plant after regeneration. The stably integrated cell division genes would confer improved cell division properties in selected tissues or environmental conditions.

Furthermore, there is the possibility that one part of the difficulty of inducing root nodules into cereals is the inability to induce the necessary localised cell division. In accordance with the present invention, additional copies of $p34^{cdc2}$ gene can, for example, be introduced into cereal crops from yeast and/or from plants. The introduced gene may be under the control of a constitutive promoter since higher levels of $p34^{cdc2}$ are not inhibitory to cell division where this has been tested in yeast. Inducible promoters may also be employed and induced only during the regeneration of transformed cells if there are unexpected difficulties from raising the basal level of $p34^{cdc2}$. It is envisaged that plants with raised basal levels of $p_{34}^{cdc2}$ or with levels raised at the time of infection with rhizobium would be more capable of forming nodules for fixation of nitrogen.

However, it may also be necessary to restrain plant cell proliferation. For example, it is sometimes the case, that a finite amount of water is available following winter rain and it is advantageous to restrain plant growth so that water resources are not exhausted before the valuable portion of the crop has developed. Wheat sown after winter rain must set grain before soil water is exhausted. Vegetative plant growth and especially transpiration of water must be restrained. Chemical agents that reduce transpiration have been found to have persisting adverse side effects on subsequent growth. The present invention proposes that reduced expression or activity of $p34^{cdc2}$ could achieve reduced growth without toxic side effects. Reduced expression or activity of $p34^{cdc2}$ may be accomplished in a number of ways, as discussed above. In one such method, a dominant-acting dose-dependent gene that restrains the activity of $p34^{cdc2}$ may be used. These are the wee-1 and mik-1 genes of fission yeast.

It is contemplated that their controlled expression will be used to modulate crop growth to take account of water resources. This would necessitate introduction of wee-1 and/or mik-1 either constitutively to create dwarfing varieties or inducibly so that dwarfing could be induced by application of inducer if there was a threat of water becoming limiting.

The present invention is also useful in other ares of control of plant growth. For example, it is frequently the case that the final size of a plant organ is determined by cell number at a critical stage of development. This applies to many important crops such as cereals, beans and apples. The present invention can be employed to stimulate cell division at this stage to increase yield.

Additionally, stimulation of canopy growth to form a cover can reduce water loss by evaporation from soil while plants remain dormant, so that more water is available when growth resumes in spring. This applies particularly to wheat sown in autumn.

Furthermore, it is desirable to promote root penetration of soil so that plants may take advantage of water that the farmer knows to be available below the surface. It is also desirable that shoot growth should not slow when water is limiting if the farmer is proposing future watering. The controls in plants produce a conservative restraint of growth at the first detection of water stress and in an agricultural situation this may limit yield. The present invention can be used to introduce copies of dominant-acting dose-dependent genes that stimulate division activity and act by influencing $p34^{cdc2}$. Two candidate genes are nim-1 and cdc 25. The other strategy is to introduce copies of mutant forms of cdc2 that do not respond to restraining modulation of activity. The two mutant forms are cdc2-1w and cdc2-3w. For all three genes, expression would be most effective if it is induced at an appropriate stage of development. One possibility would be use the nitrate reductase promoter and to induce its expression by application of dilute nitrate-containing nutrient.

This nutrient would also beneficially support the additional growth induced. Other inducers could be exploited and all are encompassed by the present invention.

Cell cycle control genes can be employed to improve growth and development in the economically valuable portions of crop plants, including both dicotyledonous plants and monocotyledonous plants. In this second taxonomic group the additional transient use of cell cycle control genes or proteins, to improve their regeneratibility, would be advantageous, but the biollistic transformation of embryogenic callus would also be a possible route for introduction of the genes.

The cell cycle control genes are employable to influence cell division behaviour at stages of development when cell number influences the final yield of economically valuable tissue. A specific example is the number of rounds of nuclear division at the multinucleate stage of endosperm development in cereal grains.

The present invention is also directed to a transgenic plant or plant cell carrying an artificially controlled cell cycle protein such as $p34^{cdc2}$ or like molecule in monocotyledonous plants, which plants include wheat, barley, oats, maize, rice or other like crop. Such an artificial control includes introduction of high constitutive or inducible promoters, multiple gene repeats and other similar procedures and techniques.

With regard to the regeneration of monocolyledonous plants, one preferred embodiment is for monocotyledonous protoplasts to be stably transformed with any beneficial gene for expression in the regenerated plant (e.g. genes for resistance to fungi or insect pests or resistance to freezing, and genes modifying division behaviour) by, for example, electroporation, with two preparations of DNA. One would carry at least a gene encoding a $p34^{cdc2}$-like molecule and perhaps additionally if necessary a cyclin-encoding gene, both under the control of constitutively expressed promoters such as 35S or its composite pEMU and lacking both a transposon element that would encourage integration and also lacking a selectable marker that would enforce the persistance of this species of DNA. This DNA would persist long enough to promote a few rounds of division and lead to microcalli in which division will continue (as it does in tissues of dividing cells from monocots although it does not in single cells of monocots, as arise after protoplasting). The other DNA to be introduced simultaneously would contain a selectable marker and an Ac element adjacent to the gene(s) that will confer new desirable properties that are to be stably introduced and expressed in the regenerated plant. The genes for stable transformation would include those for disease and pest resistance but could also include genes for improved division behaviour as hereinbefore described. In the case of monocotyledonous plants, they would be expressed under the control of endosperm of leaf meristem specific promoters.

Microcalli are obtained alive by plating transformed cells onto solid medium that contains auxin hormones (2,4-D). Microalli are then transferred to selective medium (e.g. containing antibiotic of the kanamycin type) to kill non transformed clones. Surviving clones are transferred to medium containing auxin type hormones (2,4-D NAA) and cytokinin type hormones (kinetin, BAP) and ABA for shoot and root regeneration, then hardened off and planted out for breeding. This procedure has two advantages over the alternative procedure that works with some strains of maize and perhaps rice. The alternative procedure bombards clumps of cells (derived from embryogenic callus) in suspension culture and then attempts to kill cells that have received new genetic information because they lack resistance to kanamycin or related antibiotic, that resistance being co-introduced with the DNA carrying the genes to be stably integrated. It is difficult to kill all the cells in each clump that do not have the new DNA, therefore chimaeric plants result. In the procedure outlined above, however, cells are fully dispersed as individual protoplasts thus avoiding chimaeras. The second advantage is that protoplasts give a higher incidence of true stable integration into the nuclear genome, rather than into satellite DNA, and therefore facilitates development of true breeding crops capable of transmitting the new characters to each generation.

The present invention is further described by reference to the following non-limiting Figures and Examples.

BRIEF DESCRIPTION OF THE DRAWINGS

FIG. 2 is a graphical representation showing the distribution of (A) leaf segments taken for analysis and (B) incidence of cells in the mitotic phase of division, in 90 mm long seedling leaves of wheat taken after 8 days of germination under conditions previously described. Segments 4 mm long were taken contiguously between 0 and 20 mm from the leaf base and above this at 10mm intervals. Placing of sample numbers in the diagram indicates the center of each segment. Mitotic index was determined in samples fixed in 4:1 ethanol:acetic acid and stained in acetocarmine.

A high incidence of division in the meristem region is indicated by detection of cells in this brief phase of the division cycle.

Figure 3:
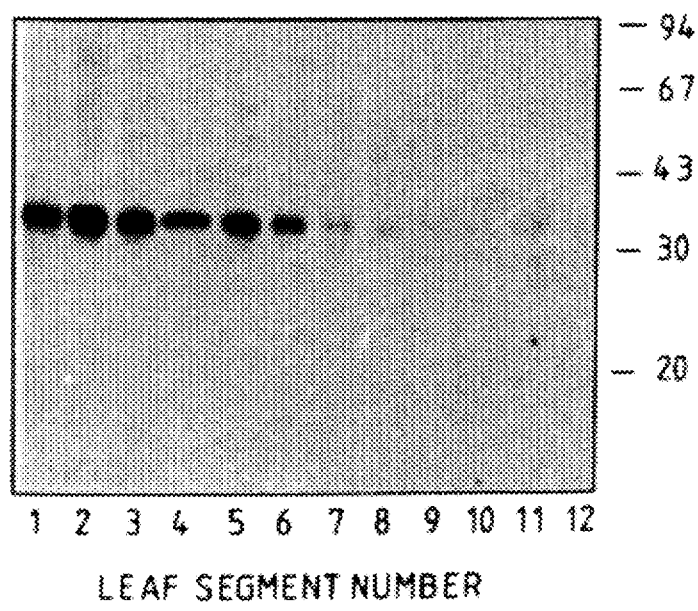

FIG. 3 is a photographic representation depicting the changes during cell differentiation, level of $p34^{cdc2}$ homologue detected in leaf segments cut as shown in FIG. 2A. Samples containing 50 μg of protein were separated by PAGE, transferred to nitrocellulose and stained with Ponceau S, then $p34^{cdc2}$ was probed with affinity-purified EGV antibody and detected using $^{125}$I-labelled anti-rabbit IgG F(ab')$_2$.

FIG. 4 is a graphical representation of the changes in amount of $p34^{cdc2}$ homologue and total protein during leaf cell development. (A) Level of $p34^{cdc2}$ protein in 50 μg samples of protein, (B) concentration of total protein in cells (total protein per gram tissue fresh mass), (C) average total protein content per cell, (D) amount of $p34^{cdc2}$ homologue per cell. Total protein in extracts made as in FIG. 1 was estimated by dye-binding, after eightyfold dilution, using ovalbumin standard. Protein per cell was calculated by multiplying the protein concentration shown in B by the average cell fresh mass, which was derived from earlier measurements of cell number and fresh mass made in this laboratory under identical conditions (5) and was confirmed by measurement of cell dimensions in these samples. Quantification of $p34^{cdc2}$ homologue on Western blots was done by probing with EGV antibody and iodinated second antibody. Complete sets of samples were processed on single panels of nitrocellulose and are, therefore, directly comparable.

Figure 5:
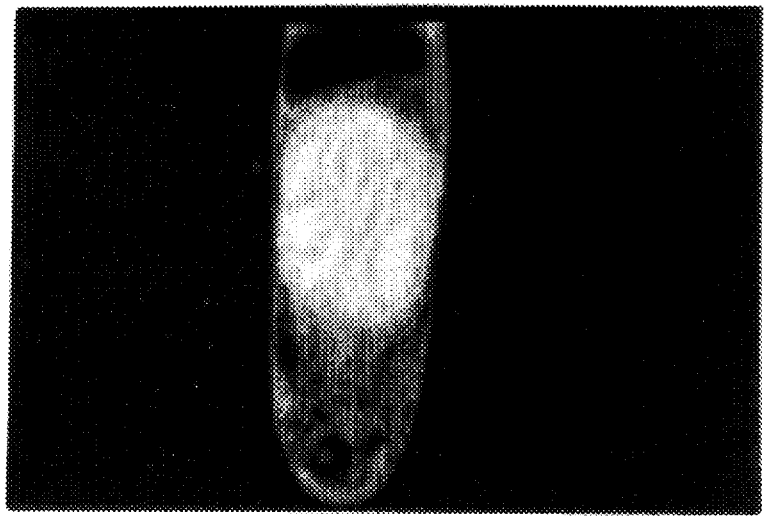

FIG. 5 is a photographic representation showing localization of $p13^{suc1}$ protein to the mitotic nucleus in live Tradescantia stamen hair cells.

The $p13^{suc1}$ protein was detected directly by excitation of a covalently linked fluorescent group (FLUOS). The protein was introduced by microinjection of a volume equal to 1% of cell volume containing 0.5 mg/ml protein in 100 mM KCl. The protein was authentic $p13^{suc1}$ encoded by the fission yeast suc 1 gene, over-expressed in *E. coli* and purified to homogeneity before fluorescent labelling.

The $p13^{suc1}$ protein, which is required for control of the mitotic activity of $p34^{cdc2}$ in fission yeast, was seen to be concentrated in the nucleus as it enters prophase of mitosis. The bright nucleus is seen occupying a third of the upper part of the cell and dark chromosomes are seen against a background of $p13^{suc1}$ fluorescence.

Figure 6:
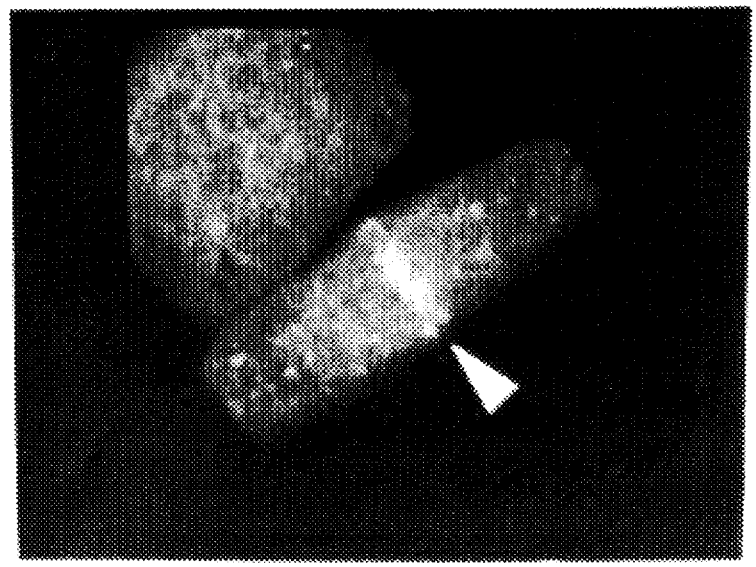

FIG. 6 is a photographic representation showing the localisation of $p34^{cdc2}$-like protein in Zinnia root tip cell.

The protein was detected using affinity purified polyclonal antibody raised against the peptide EGVPSTAIREISLLKE (SEQ ID NO:1) that has been perfectly conserved in all cell cycle control proteins related to p $34^{cdc2}$ Affinity purification employed authentic $p34^{cdc2}$ overexpressed in *E. coli*, A concentration of $p34^{cdc2}$-like protein in the preprophase band (PPB) was detected (arrowed).

Figure 7:
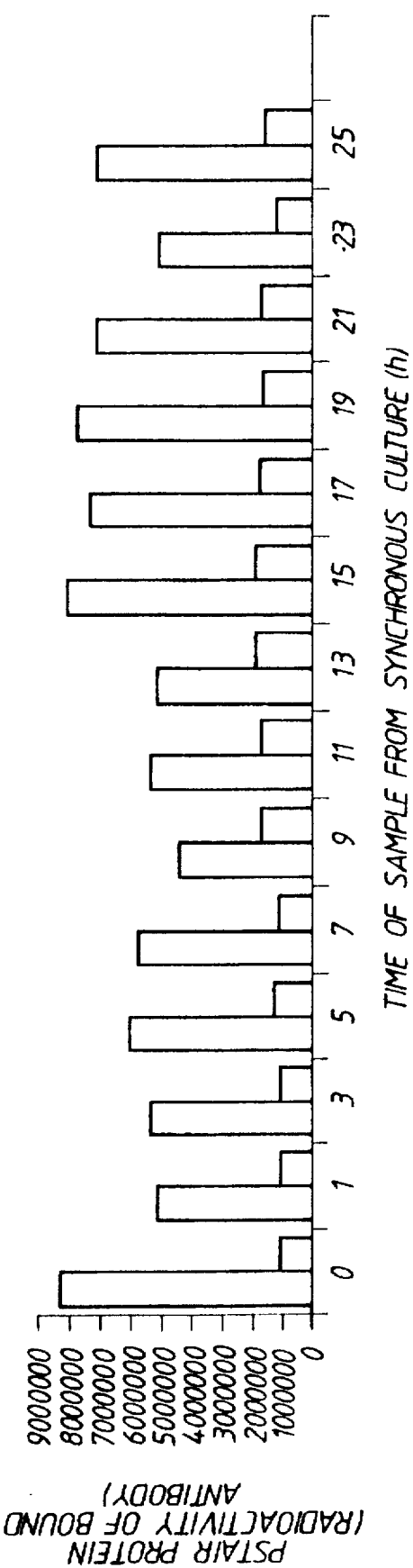

FIG. 7 is a graphical representation showing levels of $p34^{cdc2}$-like protein (PSTAIR protein) during synchronous cell division in suspension cultures of regenerable and non-regenerable *Nicotiana plumbaginifolia* cells. The regenerable cell line was capable of regenerating intact plants on transfer to solid media and the non-regenerable cells lost this ability during prolonged propagation in suspension culture. The two cell lines were grown in parallel and the protein samples from each were co-electrophoresed and levels of $p34^{cdc2}$-like protein estimated on the same Western blots.

In the pairs of samples taken at each time, that on the left derives from the non-regenerable cell line.

Each culture was sampled at intervals after release from an aphidicolin block that aligned cells at S phase and resulted in synchronous cell division on transfer to inhibitor-free medium. The non-regenerable cell line had constitutive levels of $p34^{cdc2}$-like protein that were five times those of the regenerable cell line.

Measurements of preprophase band frequency during the period 15 h to 23 h, when synchronous division was occurring in both cultures, showed that of 400 cells in the regenerable cell line 59 had phragmoplasts and 63 had preprophase bands (PPB) determining the location of the phragmoplast and future cross wall. In contrast, a much larger sample of 2000 cells from the non-regenerable cell line showed an absence of PPBs although detection of 292 phragmoplasts indicated that dividing cells were being sampled. Lack of PPBs indicates that degenerative changes during suspension culture have removed the mechanism for determining the plane of division and therefore the orientation in which new cells are formed. Such orientation is necessary for growth into a plant rather than a callus and its absence explains the non regenerability of this culture. A key feature of this invention is that it diagnoses an advantage in the controlled transient elevation of $p34^{cdc2}$-activity in transformed cells. This will avoid the need for prolonged prior propagation of cells in suspension culture to obtain a capacity for resumption of division after protoplasting. The random elevation of $p34^{cdc2}$ during suspension culture is unpredictable and usually leads to uncontrolled division and loss of capacity to regenerate plants.

FIG. 8 is a graphical representation showing levels of $p34^{cdc2}$-like protein in segments of seedling wheat leaf, measured after their transfer to solid medium containing 2,4-D for 14 days prior to assay.

Leaves from axenically grown seedlings were segmented and the proteins were fractionated by SDS-PAGE and $p34^{cdc2}$-like protein was estimated by affinity purified antibody as previously described (11).

Cells in tissue taken from the base of the leaf, which comprised the meristem cell division region, were stimulated by 2,4-D to continue synthesis of $p34^{cdc2}$-like protein and to continue division. Cells from elsewhere in the leaf had differentiated and were unresponsive to 2,4-D, did not synthesise $p34^{cdc2}$-like protein and did not divide. These mature cells survive protoplasting and can regenerate a cell wall. They would be suitable for transformation if they could be stimulated to resume cell division by introduction of cell cycle genes for transient expression.

Figure 9A:
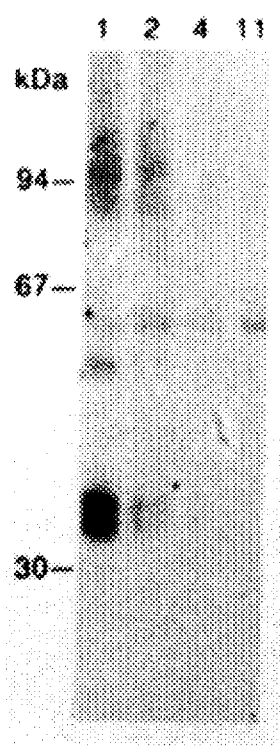

FIG. 9A is a photographic representation showing the detection of $p34^{cdc2}$-like protein in a Western blot of proteins extracted from carrot cotyledons at 1,2,4 and 11 days after germination.

Figure 9B:
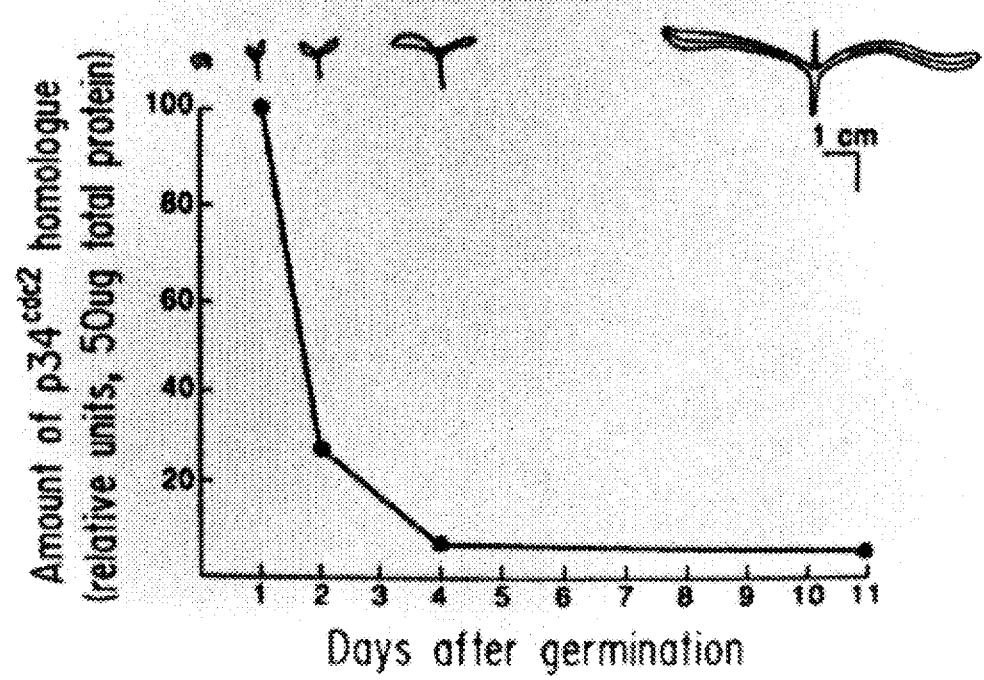

FIG. 9B is a graphical representation showing relative amounts of $p34^{cdc2}$-like protein in cotyledons at various days after germination. The stages of cotyledon and development are illustrated pictorially at each sample time. Relative units are given in Reference 12.

DETAILED DESCRIPTION OF THE INVENTION

EXAMPLE 1

MATERIALS AND METHODS

Plants

Plants were grown exactly as described in an earlier study in this laboratory (10).

Protein extraction, electrophoresis and blotting

Protein was extracted by grinding in liquid nitrogen and vigorous mixing at 0° C. with RIPA buffer containing the detergent Tween 20 and inhibitors of protease and phosphatase (6). Samples containing 50 μg of protein were separated by SDS-PAGE on a 10–15% gradient gel. The proteins were transferred to nitrocellulose and probed with anti-EGVPSTAIREISLLKE antibody (SEQ ID NO:1) that has been previously described (6; 7) after affinity purification of the antibody against mouse $p34^{cdc2}$ fusion protein (8). Control purifications without $p34^{cdc2}$ gave no reacting antibody. Bound antibody was detected with alkaline phosphatase as previously described (6) or with $^{125}$I-labelled anti-rabbit IgG F(ab')$_2$ at 0.5 mCi l– (Amersham, IM1340) employing 24h autoradiographic exposure.

Quantification of $p34^{cdc2}$ homologue $p34^{cdc2}$ homologue was quantified on Western blots by probing with EGV antibody and iodinated second antibody. Complete sets of samples were processed on single panels of nitrocellulose and are therefore directly comparable. Autoradiography was used to locate the p34 bands, which were then cut out for radioactive counting and corrected for the low backgroup (seen in FIG. 3B) that was measured in each track.

EXAMPLE 2

DETECTION OF CELL CYCLE CONTROL PROTEIN IN PLANT CELLS

Detection of p34 homologue

Figure 1:
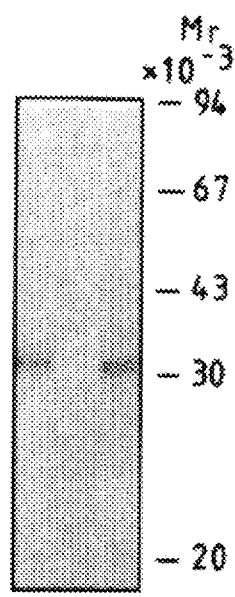
FIG. 1 is a photographic representation showing the detection of $p34^{cdc2}$ homologue in a Western blot of proteins from the cell division region of wheat leaf by probing with EGV antibody. Antibody solution was divided and preincubated, (O) without addition, (V) with 20 nM EGV peptide EGVPSTAIREISLLKE (SEQ ID NO:1)or (T) with 200 nM of altered peptide EGTPSTAIREISLMKE (SEQ ID NO:2)with substitutions at the third and fourteenth positions. The locations and sizes of markers are indicated on the right.

FIG. 1 shows that a homologue of $p34^{cdc2}$ was detected in extracts from the cell division region of wheat leaves using antibody raised against the EGVPSTAIREISLLKE sequence (SEQ ID NO:1)which has been perfectly conserved in $p34^{cdc2}$ between yeasts and humans but not in other protein kinases. After affinity purification by binding to mammalian $p34^{cdc2}$, the antibody recognised a wheat protein also of $M_r34\times10^3$. Recognition was specific for the conserved EGV peptide region since it was eliminated by competition with 20 nM EGV peptide (FIG. 1). An analogous peptide encoded by the PH085 gene, which has similarities with cc2 but no effect on cell division (9), failed to compete, indicating that the EGV antibody recognised a configuration within the largest perfectly conserved region that is specific for cell cycle function.

Distribution in leaf

Figure 4A:
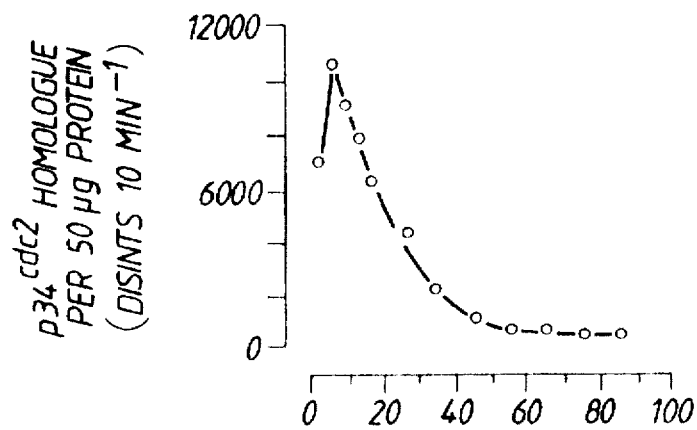
Figure 4B:
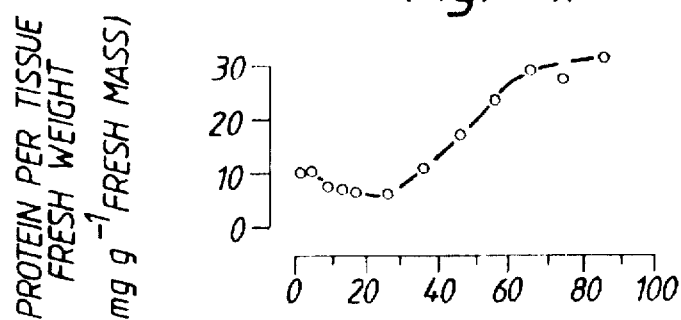
Figure 4C:
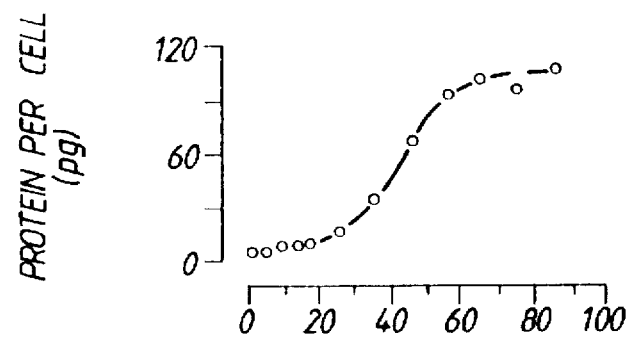
Figure 4D:
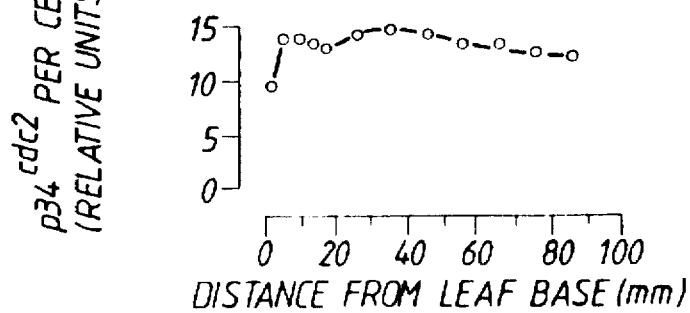

Segments were taken from base to tip of the seedling leaf (FIG. 2A) and cell division was detected only in the lower 12mm (FIG. 2B), which coincides with the region of thymidine incorporation into nuclear DNA. The changes in abundance of proteins during differentiation (FIG. 3A) are illustrated by the appearance of the $M_r55\times10^3$ subunit of RUBISCO beyond 28 mm from the base, which correlates with the increase in chloroplast number and initiation of photosynthesis. The electrophoretic mobility of $p34^{cdc2}$ homologue did not coincide with that of any of the abundant proteins and its level relative to that of other proteins declined sharply outside the region of active cell division (FIG. 3B). This decline in relative level, quantified in FIG. 4A, is due to accumulation of other proteins as differentiating cells increase in size, in protein concentration (FIG. 4B) and, therefore, in total protein content (FIG. 4C). The amount of $p34^{cdc2}$ homologue per cell (FIG. 4D) was derived by using protein content per cell to indicate how many cells yielded the protein that was probed in FIGS. 3B and 4A. No significant net breakdown of $p34^{cdc2}$ occurred during differentiation and the 94% relative decline is accounted for by cessation of its accumulation while extensive synthesis of other proteins occurs during differentiation.

EXAMPLE 3

INTERACTION BETWEEN $p34^{cdc2}$ and $p13^{suc1}$

Plant proteins considered as being like the cell cycle control protein of p34 dc2 are functionally very similar to the yeast $p34^{cdc2}$ protein. The significance of this is that there is conclusive genetical evidence in yeasts for the cell division control functions of $p34^{cdc2}$ and the similarity of the plant proteins therefore supports the probability that similar division control functions reside in them.

Such evidence includes a) Plant $p34^{cdc2}$-like protein, that has the same size of 34kDa and contains the amino acid sequence EGVPSTAIREISLLKE (SEQ ID NO:1) recognised by antibody, also binds to the yeast $p13^{suc1}$ subunit that binds to authentic yeast $p34^{cdc2}$ The bound plant protein has protein kinase activity directed against HI histone that does not require calcium or cyclic AMP and in these respects is identical with authentic yeast p3cdc2.

b) Plants contain a homologue of the $p13^{suc1}$ that is the same size as the protein from fission yeast and is recognised by antibody against yeast $p13^{suc1}$. Points (a) and (b) together indicate that the plant $p34^{cdc2}$ retains the same capacity for interaction with a regulatory protein as does the yeast enzyme. $p13^{suc1}$ is necessary in yeast for growth and for completion of anaphase in mitosis. The implication of the presence of a plant protein with homology to $p13^{suc1}$ and of the binding of plant $p34^{cdc2}$-like protein to authentic $p13^{suc1}$ is that plant $p34^{cdc2}$ is regulated by interaction with other proteins of the network that was first characterised in yeasts as we proposed in our patent.

These results are disclosed in John et al (11) which is herein incorporated by reference.

EXAMPLE 4

This example is directed to the study of whether (i) the intracellular locations of proteins that interact with $p34^{cdc2}$- and (ii) the intracellular location of $p34^{cdc2}$ relative to potential target proteins, is consistent with function of $p34^{cdc2}$ in the plant cell cycle.

a) The 13kDa protein $p13^{suc1}$ of the fission yeast has been over expressed in E. coli, purified to homogeneity, labelled covalently with the fluorescent dye 5(6)-carboxyfluorescein-N-hydroxysuccinimidester and microinjected at 0.5mg/ml into live Tradescantia stamen hair cells that were actively dividing. The protein becomes concentrated in the nucleus at prophase of mitosis (FIG. 5), which is consistent with the proposal that $p34^{cdc2}$ functions at mitosis in plants and is regulated by association with regulatory subunits such as $p13^{suc1}$.

b) The location of $p34^{cdc2}$-like protein has been determined by antibody binding and immunofluorescence microscopy in dividing plant cells.

The protein is located in the cytoplasm and nucleus but at early mitoses becomes localised at a major determinant of the orientation of division, which is a cytoskeletal structure called the pre-prophase band (PPB) of microtubules (see FIG. 6). The PPB marks the site of the orientation of the cross wall that separates the new (daughter) cells and hence determines the direction in which growth occurs. Regulatable $p34^{cdc2}$ levels and capacity to form PPBs are both key elements in the capacity to regenerate plants from cultured cells. Such regeneration is necessary if introduced genetic information is to be exploited in crop improvement. The dual requirement for p34$^{cdc2}$ levels and capacity to form PPBs are both key elements in the capacity to regenerate plants from cultured cells. Such regeneration is necessary if introduced genetic information is to be exploited in crop improvement. The dual requirement for p34$^{cdc2}$ regulation and PPB formation is emphasised by the co-location of the two elements.

A related line of investigation has sought to establish whether other proteins that are necessary for p34$^{cdc2}$ function in other kingdoms are present in plants. Polymerase chain reaction (PCR) techniques were used to amplify regions of plant genes that are homologous with cell cycle control genes. In wheat, genetic information was detected that can encode a p34$^{cdc2}$ like protein and also a protein like the G class of cyclins that complex with p34$^{cdc2}$ in G1 phase and have been suggested to activate its functions in the G1 phase of the cell cycle. The presence of this portion of a G1 cyclin gene and the potential for using it to clone monocotyledonous cyclins using the PCR amplified fragment as a probe is significant since monocotyledonous cells commonly arrest division in G1 phase of the cell cycle and a suitable cyclin will assist in stimulating division.

Another approach has been to directly investigate the molecular basis of the loss of regenerability that occurs in suspension cultures of plant cells.

Prolonged culture of plant cells in suspension involves repeated dilution with fresh medium and the gradual predominance of cells that divide more rapidly under those unnatural conditions. The inventors observed in suspension cultures of Nicotiana plumbaginifolia that the continued selection for faster dividing cells that unavoidably occurs each time the culture is diluted results in increased levels of p34$^{cdc2}$ and loss of pre prophase bands (detailed in FIG. 7).

The restraint of cell division was investigated in mature cereal leaf cells is due to failure to induce the key cell division protein p34$^{cdc2}$. Although tissue was taken from the actively dividing (meristem) region, when cultured axenically on medium containing 2,4-D, cells retain p34$^{cdc2}$-like protein at levels capable of supporting division (see FIG. 9), whereas tissue taken from elsewhere in the leaf containing mature cells with low levels of p34$^{cdc2}$-like protein was unable to raise the levels of p34$^{cdc2}$ (see FIG. 8) and was unable to initiate cell division. The meristem tissue that readily continues cell division is unsuitable as a source for transformation because they yield protoplasts that do not regenerate a cell wall and so are unable to resume cell division after introduction of genetic material. Mature cells can regenerate a cell wall but a major restraint of division in mature cells, if they have not been subject to prolonged suspension culture, is their retention of low levels of p34$^{cdc2}$ protein.

REFERENCES

1. Nurse, P. and Bisset, Y. *Nature* 292: 558–560, 1981.
2. Nurse, P. and Fantes, P. *The Cell Cycle* pp85–98, 1981.
3. Russell, P. and Nurse, P. *Cell* 49: 569–576, 1987.
4. Moreno, S., Nurse, P. and Russell, P. *Nature* 344: 549–552, 1990.
5. Wernicke, W and Milkovits, L. *Physiologia Pl.* 69 23–28, 1987b.
6. John, P. C. L., Sek, F. J. and Lee, G. M. *Plant Cell* 1; 1185–1193, 1989.
7. Lee, M. G. and Nurse, P. *Nature* 327: 31–35, 1987.
8. Snyder, M., Elledge, S., Sweetser, D., Young, R. A. and Davis, R. W. *Meth, Enzym,* 154: 107–128, 1987.
9. Toh-EA., Tanaka, K., Uesono, Y. and Wickner, R. B. *Saccharomyces Cerevisiae. Molec. Gen Genet,* 214: 162–164, 1988.
10. Wernicke, W. and Milkovits, L. *Physiologia Pl.* 6: 16–22, 1987.
11. John, P. C. L., Sek, F. J. and Hayles, J. *Protoplasma* 161: 70–74, 1991.
12. Gorst, J. R., Sek, F. J. and John, P. C. L. *Planta* 1: 304–310, 1991.

---

What is claimed:

1. A transgenic plant transformed with at least one of a coding sequence for $p_{34}{}^{cdc2}$, a coding sequence for a $p34^{cdc2}$-like protein having a cyclin related kinase function, or a regulatory element which interacts with and modulates the level (of $p34^{cdc2}$ or $p34^{cdc\,2}$-like molecule wherein said regulatory element is selected from the group consisting of $p13^{suc1}$, cyclin, cdc25 or products of nim-1, wee-1 and mik-1 genes and wherein said transgenic plant expresses enhanced levels of $p34^{cdc2}$ or $p34^{cdc2}$-like protein.

2. A transgenic plant according to claim 1 wherein said transgenic plant is a monocotyledonous plant.

3. A transgenic plant according to claim 1 wherein said a dicotyledonous plant.

4. A transgenic plant according to claim 1 wherein said monocotyledonous plant is Tradescantia, wheat, barley, oats, maize, or rice.

* * * * *

UNITED STATES PATENT AND TRADEMARK OFFICE
CERTIFICATE OF CORRECTION

PATENT NO. : 5,750,862
DATED : May 12, 1998
INVENTOR(S) : Peter C. L. John

It is certified that error appears in the above-identified patent and that said Letters Patent is hereby corrected as shown below:

On the title page, Item [56], under "OTHER PUBLICATIONS", Column 2, line 28: "p80$_{cdc25}$" should read --p80$_{cdc25}$ Column 1, line 15: "specialised" should read --specialized--
Column 1, line 15: "specialization" should read --Specialization--
Column 2, line 16: "By" should begin a new paragraph.
Column 2, line 19: "derivatisation" should read --derivatization--
Column 3, line 14: "specialised" should read --specialized--

Column 3, line 20: after "p34$^{cdc2}$" insert --.--
Column 3, line 46: "localised" should read --localized--
Column 4, line 38: "p$_{34}$" should read --p34--

Column 4, line 66: "ares" should read --areas--
Column 7, line 53: "E. coli," should read --E. coli.--

Column 9, line 14: "1-" should read --1$^{-1}$--
Column 9, lines 35 & 41: "recognised" should read --recognized--

Column 9, lines 36 & 50: "103" should read --10$^3$--

Column 9, line 40: "cc2" should read --cdc2--

UNITED STATES PATENT AND TRADEMARK OFFICE
CERTIFICATE OF CORRECTION

PATENT NO. : 5,750,862
DATED : May 12, 1998
INVENTOR(S) : Peter C.L. John

It is certified that error appears in the above-identified patent and that said Letters Patent is hereby corrected as shown below:

Column 10, line 5: "p34 dc2" should read --p34 $^{cdc2}$ --
Column 10, line 12: after "includes" insert --:--
Column 10, lines 15 & 24: "recognised" should read --recognized--

Column 10, line 17: after "p34$^{cdc2}$" insert --.--

Column 10, line 21: "p3cdc2." should read --p34$^{cdc2}$ --
Column 10, line 59: "The protein..." should continue on line 58.
Column 10, line 61: "localised" should read --localized--
Column 11, line 8: "emphasised" should read --emphasized--
Column 13, line 12, Claim 1: "p$_{34}$ should read --p34--

Column 13, line 15, Claim 1: "(of" should read --of--
Column 14, line 12, Claim 2: "said a" should read --said transgenic plant is a--

Signed and Sealed this

Twenty-seventh Day of July, 1999

Attest:

Q. TODD DICKINSON

*Attesting Officer*      Acting Commissioner of Patents and Trademarks